United States Patent
Machado et al.

(10) Patent No.: US 9,981,123 B2
(45) Date of Patent: May 29, 2018

(54) LEAD ASSEMBLIES WITH ADJUSTABLE CONTACTS

(71) Applicant: THE CLEVELAND CLINIC FOUNDATION, Cleveland, OH (US)

(72) Inventors: Andre G. Machado, Beachwood, OH (US); Mark S. Lobosky, Chardon, OH (US); Karl West, Cleveland, OH (US); Scott Lempka, Cleveland Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days. days.

(21) Appl. No.: 15/611,358

(22) Filed: Jun. 1, 2017

(65) Prior Publication Data
US 2017/0266435 A1  Sep. 21, 2017

Related U.S. Application Data

(62) Division of application No. 14/726,783, filed on Jun. 1, 2015.

(60) Provisional application No. 62/004,932, filed on May 30, 2014.

(51) Int. Cl.
| *A61N 1/00* | (2006.01) |
| *A61N 1/05* | (2006.01) |
| *A61N 1/372* | (2006.01) |
| *A61N 1/368* | (2006.01) |
| *A61N 1/36* | (2006.01) |

(52) U.S. Cl.
CPC ......... *A61N 1/0551* (2013.01); *A61N 1/3686* (2013.01); *A61N 1/36182* (2013.01); *A61N 1/37235* (2013.01)

(58) Field of Classification Search
CPC .............. A61N 1/0551; A61N 1/36182; A61N 1/3686; A61N 1/37235
See application file for complete search history.

(56) References Cited

U.S. PATENT DOCUMENTS

| 5,824,030 A * | 10/1998 | Yang ...................... A61N 1/056 600/374 |
| 7,463,927 B1 * | 12/2008 | Chaouat ............. A61N 1/36071 607/46 |
| 7,769,470 B1 | 8/2010 | Rezai |

(Continued)

OTHER PUBLICATIONS

Hill, United States Statutory Invention Registration, Reg. No. H1,905, Published Oct. 3, 2000.

(Continued)

*Primary Examiner* — Lindsey G Wehrheim
(74) *Attorney, Agent, or Firm* — Tarolli, Sundheim, Covell & Tummino LLP

(57) ABSTRACT

One aspect of the present disclosure relates to lead assemblies for stimulating tissue. The lead assemblies can include lead bodies that are slidably coupled to each other and include one or more contacts that are moveably disposed within the slits of the lead bodies. The positions of the one or more contacts can be adjusted to change the direction of stimulation. For example, the positions of the one or more contacts can be adjusted based on theoretically-optimal positions determined from a patient-specific computer model. Parameters of the stimulation applied by the one or more contacts can also be optimized based on the patient-specific computer model.

10 Claims, 9 Drawing Sheets

(56) References Cited

U.S. PATENT DOCUMENTS

| | | |
|---|---|---|
| 7,831,308 B2 | 11/2010 | Rezai |
| 2002/0183817 A1 | 12/2002 | Van Venrooij |
| 2005/0288760 A1 | 12/2005 | Machado |
| 2009/0105776 A1* | 4/2009 | Aldridge ............ A61B 5/04001 607/2 |
| 2009/0204192 A1 | 8/2009 | Carlton |
| 2010/0082086 A1 | 4/2010 | Zhu |
| 2011/0009927 A1 | 1/2011 | Parker |
| 2012/0071936 A1 | 3/2012 | Pianca |
| 2012/0153967 A1 | 6/2012 | Koop |

OTHER PUBLICATIONS

International Search Report and Written Opinion for PCT/US2015/033479, dated Aug. 31, 2015, pp. 1-9.

* cited by examiner

LEAD ASSEMBLIES WITH ADJUSTABLE CONTACTS

RELATED APPLICATIONS

This application is a divisional of U.S. patent application Ser. No. 14/726,783, filed Jun. 1, 2015, and entitled "LEAD ASSEMBLY WITH ADJUSTABLE CONTACTS", which claims the benefit of U.S. Provisional Application No. 62/004,932, filed May 30, 2014, and entitled "ELECTRICAL LEAD ASSEMBLIES WITH ADJUSTABLE ELECTRODES." These applications are hereby incorporated by reference in their entirety for all purposes.

TECHNICAL FIELD

The present disclosure relates generally to lead assemblies having at least one contact whose position in the lead can be adjusted.

BACKGROUND

Neural modulation applications generally rely on leads that include contacts that are disposed in a fixed position within the lead body. The leads can be implanted at a location in a region of interest in a patient's body and surgically stabilized at the location. Typically, the region of interest can include neural elements, some of which are intended to be affected by stimulation ("desired elements") and other neural elements ("undesired elements") that, when inadvertently stimulated, can cause unwanted effects. The desired elements and undesired elements can be located in close proximity so that the stimulation, although intended for the desired elements, can spread to affect the undesired elements.

Once the lead is surgically stabilized in the location, scar tissue can forms over the lead. Accordingly, much of the programming of the electrical lead is done after the surgery is completed and after the patient has healed from the surgical procedure. Several programming strategies exist to decrease the stimulation of the undesired elements. Such strategies include adding multiple (and smaller) electrical contacts (electrodes) to the lead body so that the site(s) of neural tissue receiving electrical stimulation can be changed by deactivating electrode contacts that produce side effects and activating electrode contacts that predominantly produce the intended effects. In addition, it is possible to change other stimulation parameters such as the polarity, frequency, and/or pulse width. In addition, other technological modifications include "current steering" and directional electrical contacts. Current steering includes fractionating the current, as well as selectively delivering the current in a particular direction using "directional" deep brain stimulation ("DBS") leads. Directional DBS leads have electrical contacts that partially cover one segment of a cylindrical lead, aimed at favoring the effects of stimulation to one side of the lead while sparing the other side.

With respect to spinal cord stimulation or cortical stimulation, a few millimeters of difference in the contact positioning over the spinal cord or cortex (epidurally or subdurally) can affect which neural elements are stimulated. Thus far, this limitation has been addressed by designing leads with more contacts or increasing the density of contacts on the lead body. An issue with high density leads, such as paddle leads with 16 or 32 electrical contacts (particularly relating to epidural stimulation), is that the cushion of cerebrospinal fluid (CSF) between the lead and the spinal cord or cortex "washes" or "blurs" the precision of such higher density leads. For example, the short distance between the several small electrical contacts of such leads can result in no difference from one electrical contact to the other effectively resulting in stimulation of the desired and undesired neural elements. This is the case because in order to achieve effective spinal cord or brain cortical stimulation, the voltage of the electrical current has to be ramped to a point that the sphere of stimulation is so large that minor changes in electrical contact position do not effectively alter which neural elements of the spinal cord will be affected. In addition, the cerebrospinal fluid cushion is highly conductive, further washing out minor differences is electrical fields generated by small adjacent electrical contacts.

With respect to deep brain stimulation, there are several possible applications already in practice and under investigation, including deep brain stimulation for Alzheimer's disease, stroke rehabilitation, depression, obsessive-compulsive disorder, epilepsy, tremor and Parkinson's disease. Lead location is critically associated with outcome. Because deep brain structures are often small and in tight proximity with other structures, it is important to favor stimulation towards the desired structures only. While directional leads can help with that (as well as current steering), little can be done to change the orientation of the directional leads once the implant procedure is completed and the patient has healed.

While these programming strategies each have some utility, they each have limitations. The best scenario remains implanting the lead so that the contacts are in an ideal position for stimulation, eliminating the need for such programming strategies. However, little can be done to change the orientation of the contacts once the patient has healed from the implantation procedure. Further, it would be desirable to have larger contacts implanted in the ideal location rather than the small contacts built into high density leads.

SUMMARY

The present disclosure relates generally to lead assemblies having one or more contacts whose positions in the lead can be adjusted. For example, the positions of the one or more contacts within the lead can be adjusted based on a determination of theoretically-optimal positions from a patient-specific computer model. Parameters of the stimulation applied by the one or more contacts can also be optimized based on the patient-specific computer model.

According to an aspect, the present disclosure provides a lead assembly for stimulating tissue. The lead assembly includes a first lead body including a first slot arranged in a first orientation and a second lead body including a second slot corresponding to the first slot and having a second orientation. The first lead body is slidably coupled to the second lead body. The lead assembly further includes an electrical contact moveably disposed in the first slot and the corresponding second slot. The assembly also includes an energy source electrically connected to the electrical contact for providing electrical energy to stimulate the tissue. An actuator is in operable communication with the first lead body, the second lead body, or both to cause sliding relative movement between the lead bodies which results in movement of the electrical contact.

According to another aspect, the present disclosure provides a system including a lead assembly coupled to a computing device. The lead assembly can include a moveable contact at a first position and an actuator to move the contact from the first position to a second position. The computing device can be in operative communication with the actuator and can include memory storing computer-executable instructions and a processor to access the memory and execute the computer-executable instructions to at least: define a theoretically-optimal contact location based on a patient-specific computer model and send an instruction to the actuator to move the moveable contact to the second position representing the theoretically-optimal contact location.

According to a further aspect, the present disclosure provides a method for optimizing a location of a moveable contact within a lead after implantation. The method can be implemented by a system comprising a processor. The method can include receiving a location of a lead implanted in a patient's body. Based on the location of the lead in the patient's body and a patient-specific computer model, a theoretically-optimal location for a moveable contact within the lead can be determined. An instruction can be provided to an actuator of the lead to move the moveable contact from a first position to a second position representing the theoretically-optimal location.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
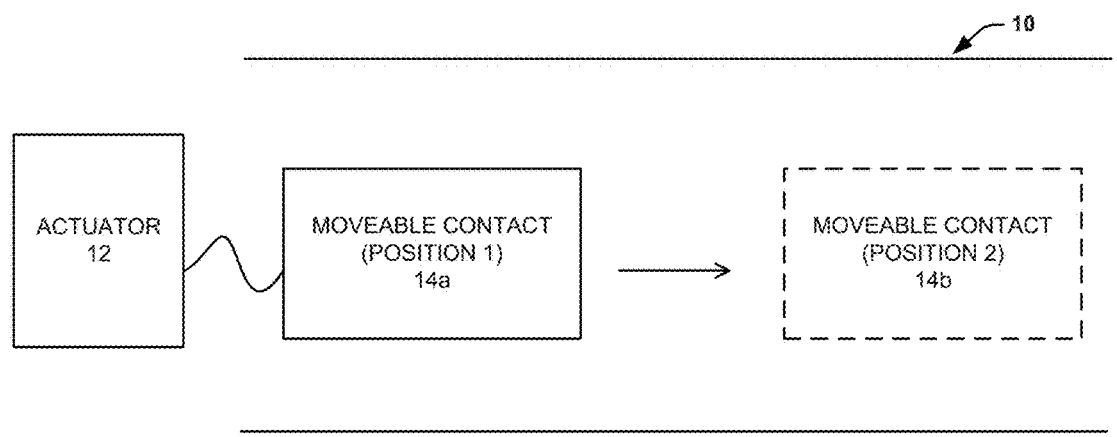
FIG. 1 is a block diagram of an example lead assembly with a moveable contact according to an aspect of the present disclosure.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

In addition, it will be understood that when an element is referred to as being "on," "attached" to, "connected" to, "coupled" with, "contacting," in "communication" with etc., another element, it can be directly on, attached to, connected to, coupled with, contacting, or in communication with the other element or intervening elements may also be present. In contrast, when an element is referred to as being, for example, "directly on," "directly attached" to, "directly connected" to, "directly coupled" with, "directly contacting," or in "direct communication" with another element, there are no intervening elements present.

It will also be appreciated by those of skill in the art that references to an element that is disposed "adjacent" another element may have portions that overlap or underlie the adjacent element.

As used herein, the term "lead assembly" refers to an implantable device that includes one or more moveable contacts for stimulation of a portion of a patient's body. The lead assembly can have any shape as long as the location of at least one of the moveable contacts can be adjusted.

As used herein, the term "moveable contact" refers to an element that can deliver the stimulation to at least a portion of a target tissue. The moveable contact can have an adjustable position.

As used herein, the term "stimulation," "stimulated," "activation," and "activated" refer to any artificial input that causes one or more neuromodulatory effects (e.g., excitation/activation, inhibition, conduction block, modulation of response to other inputs, or the like) in at least a portion of neurons in a target tissue. The stimulation can be electrical stimulation, magnetic stimulation, optical stimulation, thermal stimulation, electromagnetic stimulation, or the like. In some instances, the target tissue can be neural tissue, such as a portion of the brain, the spinal cord, the peripheral nervous system. In other instances, the target tissue can be another electrically conductive tissue, such as cardiac tissue, muscle tissue, or the like. Accordingly, the lead assembly can be used for deep brain stimulation, cortical stimulation, spinal cord stimulation, peripheral nerve stimulation, muscular stimulation, cardiac stimulation, or the like.

As used herein, the term "patient" refers to any warm-blooded organism including, but not limited to, a human being, a pig, a rat, a mouse, a dog, a cat, a goat, a sheep, a horse, a monkey, an ape, a rabbit, a cow, etc.

As used herein, the term "substantially" used with respect to certain geometric shapes or orientations means that the shape or orientation of the element need not have the mathematically exact described shape or orientation but can have a shape or orientation that is recognizable by one skilled in the art as generally or approximately having the described shape or orientation.

As used herein, the term "corresponding to one" encompasses the term "corresponding to at least one".

As used herein, the terms "left," "right," "medial," "lateral," "caudal," and "cranial" refer to anatomical directions and orientations of a human patient in a standard anatomical position as is known in the art.

II. Overview

The present disclosure relates generally to a lead assembly. For example, the lead assembly can be used in a variety of surgical procedures where it is desired to deliver stimulation to a target tissue to achieve a therapeutic effect. The lead assembly can have one or more moveable contacts, whose positions in the lead can be adjusted after the lead has been implanted. Depending on the location of the lead in the region of interest and depending on effects noted during programming, one or more of the moveable contacts can be moved in one or more directions to favor stimulation of the intended elements in the target area to achieve the intended effects, while sparing stimulation of non-intended elements to achieve non-intended effects. As such, the lead assemblies with adjustable contacts can use a patient-specific computer model to better position the contacts to provide more targeted and focal stimulation of intended tissue to achieve the desired therapeutic effect even after the patient has healed from the procedure for surgical implantation and scar tissue has developed around the lead.

III. Lead Assembly

One aspect of the present disclosure can include a lead assembly 10 as shown in FIG. 1. The lead assembly 10 can be used for stimulating tissue within a target area with at least one moveable contact 14a. The orientation of the moveable contact can be changed (e.g., from position 1 to position 2) after implantation of the lead assembly 10 within a patient's body. The adjustment of the contact can be facilitated by an actuator 12.

In some instances, the actuator 12 can be operatively coupled to a computing device to receive an instruction to move the contact to a new position. In some instances, the instruction to move the contact can be based on a determination, by the computing device, of an optimal position for the contact from a patient specific computer model. In other instances, the instruction to move the contact can be based on an instruction from a component other than the computing device (e.g., a doctor) based on observations of an output of a computing device. Accordingly, the computing device can control not only the characteristics of the pulses and which contacts are activated, but can also control the position of the moveable contact 14a within the lead assembly 10. If a patient is implanted with the lead assembly 10 and is having stimulation of a neural element that is lateral to the intended neural element, for example, the moveable contact 14a can physically move to a new location 14b in order to facilitate stimulation of a greater number of intended elements while sparing the more unintended elements from stimulation.

In some instances, the lead assembly can include a plurality of contacts, with some of the plurality moveable. In other instances, the lead assembly 10 can include a plurality of moveable contacts. Additionally, in some instances, the lead assembly 10 can be covered, in at least a portion, by a film that prevents scar tissue from being formed around the lead assembly 10.

Figure 2:
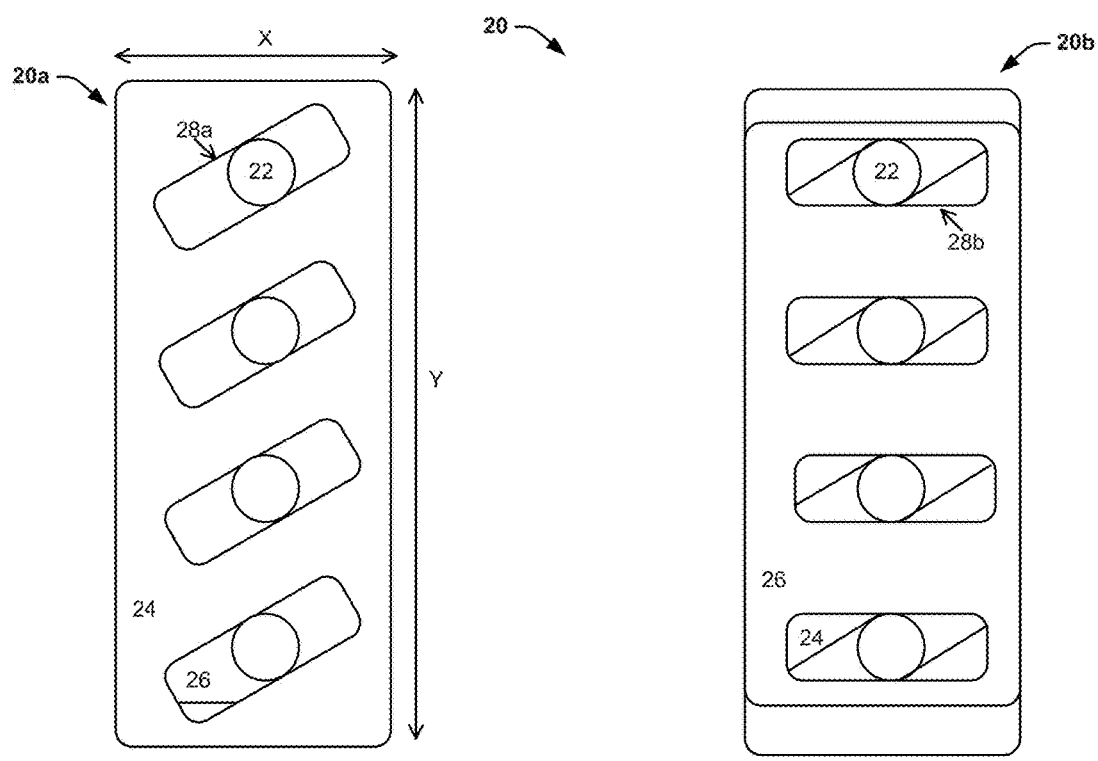
FIG. 2 includes planar view of the front and back of an example lead assembly.

The lead assembly 10 can have a number of different configurations that allow the position of at least one moveable contact to be adjusted so that energy can be delivered to target tissue of a patient's body. A front view 20a and back view 20b of an example configuration of a lead assembly with a paddle-like shape are shown in FIG. 2. It will be understood that the lead assembly can have a different configuration than the one illustrated and described as long as it has at least one moveable contact.

The lead assembly, as exemplified by front view 20a, can include a first lead body 24 that can include a first slot 28a arranged in a first orientation. A second lead body 26, as exemplified by back view 20b, can include a second slot 28b that can correspond to the first slot 28a and have a second orientation. The lead bodies 24, 26 can be slidably coupled to one another to allow the position of a moveable contact 22, which can be moveably disposed in the first slot 28a and the corresponding second slot 28b, to be adjusted. The first lead body 24 and/or the second lead body 26 can have a degree of flexibility to facilitate implementation of the lead assembly. For example, the first lead body 24 and/or the second lead body 26 can be constructed from a material, like nitinol, with a degree of flexibility that can be controlled through the design of the device offering the material in the martensitic through the austenitic superelastic state.

In some instances, as illustrated in FIG. 2, the lead assembly 20 can include a plurality of first slots corresponding to a plurality of second slots, housing an array of a plurality of moveable contacts 22 therein. Although FIG. 2 shows four slot pairs and moveable contacts, it will be understood that a greater or fewer number of slot pairs and moveable contacts can be included in the lead assembly. In some instances, components of each of the plurality slot pairs corresponding to the same lead body 24, 26 can have the same orientation. In other instances, at least one component of each of the plurality slot pairs corresponding to the same lead body 24, 26 can have a different orientation than other components. For example, as depicted in FIG. 2, each of the plurality of first slots 28a is substantially diagonal and each of the plurality of second slots 28b is substantially horizontal. However, the plurality of first and second slots can have other orientations as long as the respective contact disposed therein is able to move therein, such as move laterally, medially, cranially, and/or caudally, for example.

An energy source can be electrically connected to the moveable contact 22, which can provide energy from the energy source to the tissue. For example, the energy source can provide electrical energy, magnetic energy, optical energy, thermal energy, or the like to the moveable contact 22 for application to the tissue. In some instances, the energy source can include any suitable device that can provide energy to the contacts such as an implantable pulse generator, a battery, or a wireless external transmitter.

An actuator can be in operable communication with the first lead body 24, the second lead body 26, or both to cause sliding relative movement between the lead bodies, which can result in movement of the moveable contact 22. In some instances, the actuator 12 can be a piston/cylinder mechanism, a pneumatic actuator, a hydraulic actuator, a piezoelectric actuator, a shape memory actuator, or an electromechanical actuator.

The first orientation and the second orientation of the first slot 28a and the second slot 28b, respectively, can be the same or different as long as the moveable contact 22 is able to move in some direction upon activating the actuator that is suitable for the associated application. For example, the moveable contact can move lateral to medial; medial to lateral; caudal to cranial; anterior to posterior; cranial to caudal; and/or can rotate around the major or minor axis of the lead body. Further, the moveable contact 22 can move any suitable distance bound by the size of the lead assembly. The moveable contact 22 can be a single contact or a plurality of contacts. In the case of a plurality of contacts, the position of some or all of the contacts can be adjusted.

In the example illustrated in FIG. 2, the lead bodies are plates and the contacts can move as the first plate 24 is activated by the actuator to move along the Y-axis. For example, when the first plate 24 is activated downward or in a caudal direction, the contacts can be skewed to the left. In another example, when the first plate 24 is centered vertically, the contacts can be positioned vertically. In a further example, when the first plate 24 is activated upward or in a cranial direction, the contacts can be skewed to the right. Of course, instead of the first plate being activated by an actuator, the second plate could be activated by an actuator in the reverse direction to achieve the same moveable contact positioning.

Figure 3:
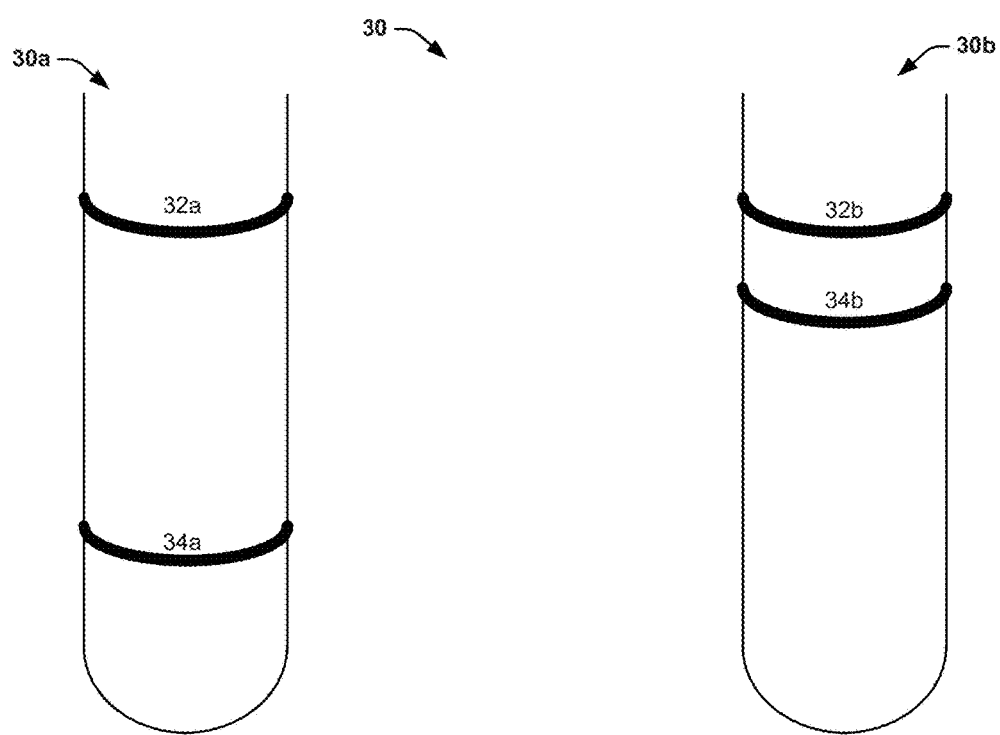
FIGS. 3 and 4 are illustrations example lead assemblies with contacts in an original position and in a new position after re-positioning.
Figure 4:
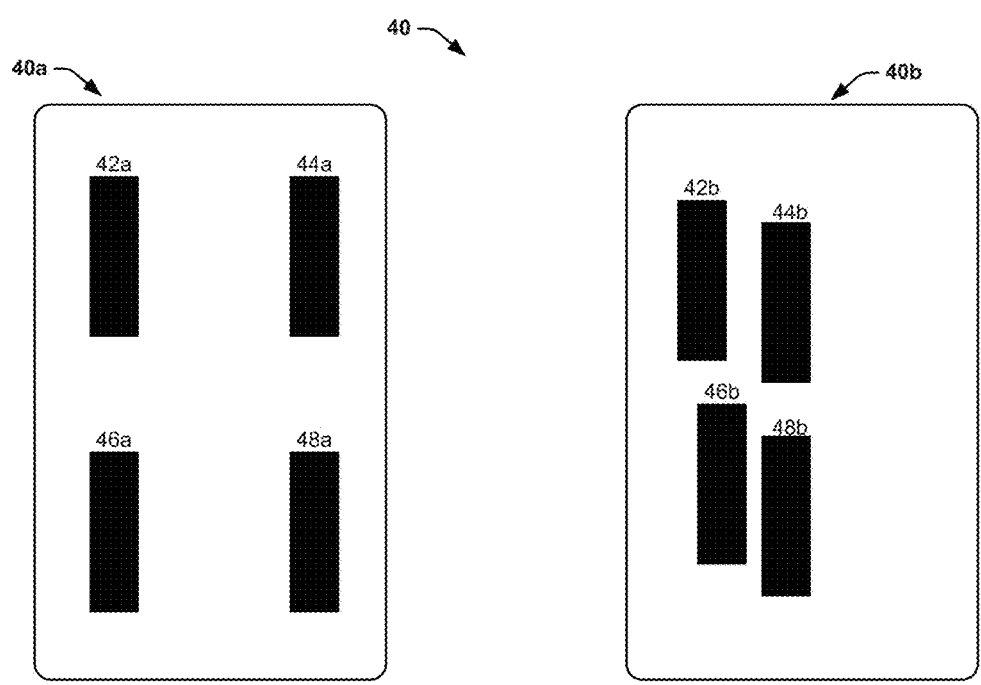

FIGS. 3 and 4 illustrate examples of lead assemblies 30 and 40 with contacts in a first orientation 30a, 40a and in a second orientation 30b, 40b after re-positioning. FIGS. 3 and 4 show different example configurations of the lead assembly. For example, FIG. 3 illustrates a cylindrical lead assembly, while FIG. 4 illustrates a paddle lead assembly. In each case, the lead assemblies can include a first plate 24, a second plate 26, and one or more moveable contacts 22 with similar functionality to that described with respect to FIG. 2.

In the example of FIG. 3, in the first orientation 30a, two moveable contacts 32a and 34a are illustrated. In the second orientation 30b, the first moveable contract 32b stays in its original position, but the second moveable contact 34b moves to a new location. In the example of FIG. 4, in the first orientation 40a, four moveable contacts 42a, 44a, 46a, 48a are illustrated. In the second orientation 40b, all four of the moveable contacts 42b, 44b, 46b, 48b move to new locations. It will be understood that the contacts can move in any direction that is the same or different from these examples.

IV. Systems

Figure 5:
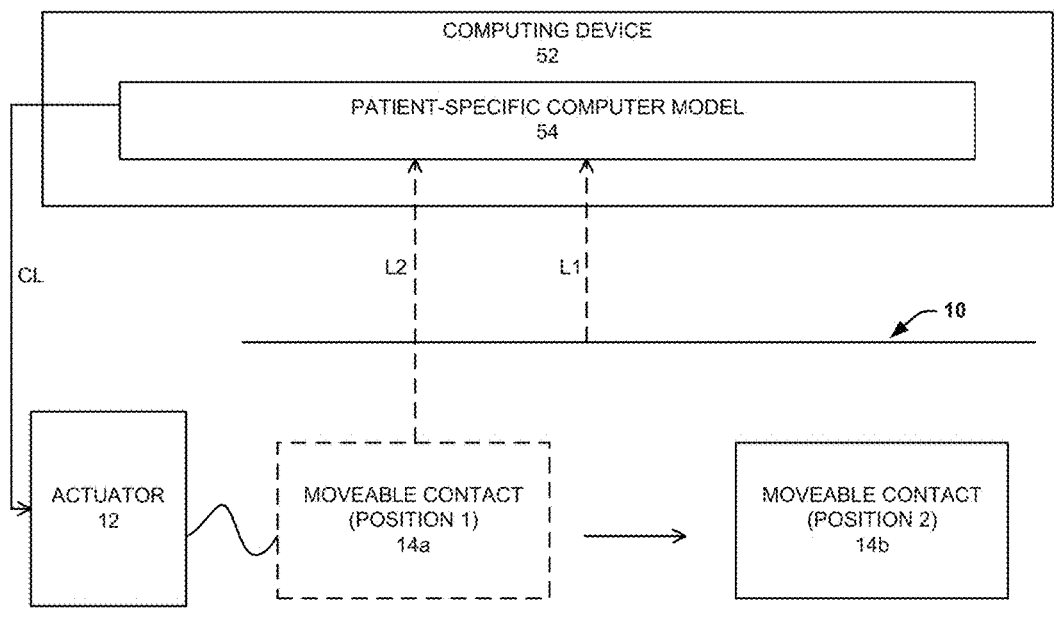
FIG. 5 is a block diagram of a system that can reposition a moveable contact within a lead assembly according to another aspect of the present disclosure.

Another aspect of the present disclosure can include a system, as illustrated in FIG. 5, which can reposition a moveable contact within a lead assembly 10. The system can include the lead assembly 10, an actuator 12, and a computing device 52 with a patient-specific computer model 54. The computing device 52 and the actuator 12 can be communicatively coupled together (CL) so that the computing device 52 can send an instruction to the actuator 12 and the actuator 12 can facilitate the movement of the moveable contact from position 1 14a to position 2 14b. In some instances, the computing device can receive feedback from the lead assembly L1 and/or the moveable contact L2.

In some instances, the computing device 52 can utilize a non-transitory memory to store computer-executable instructions and a processor to execute the computer-executable instructions to facilitate the performance of operations and/or implement the functions of one or more components of the computing device 52. The computing device 52 can be, for example, a general purpose computer, special purpose computer, and/or other programmable data processing apparatus. Accordingly, the computer-readable medium can be any non-transitory medium that is not a transitory signal and can contain or store the program for use by or in connection with the instruction or execution of a system, apparatus, or device. The computer-readable medium can be, for example but not limited to, an electronic, magnetic, optical, electromagnetic, infrared, or semiconductor system, apparatus or device. More specific examples (a non-exhaustive list) of the computer-readable medium can include the following: a portable computer diskette; a random access memory; a read-only memory; an erasable programmable read-only memory (or Flash memory); and a portable compact disc read-only memory.

The computing device 52 can define theoretically-optimal location for the moveable contact based on execution of the patient-specific computer model 54. The definition of the theoretically-optimal location can be made either prior to implantation of the lead assembly 10 or after implantation of the lead assembly 10 (e.g., prior to programming the lead assembly 10 and/or prior to re-programming the lead assembly 10). In some instances, the computing device 52 can also define theoretically-optimal stimulation parameters based on the location of the lead assembly 10 upon implantation and/or the position of the moveable contact 14 within the lead assembly 10 either before or after implantation. In some instances, the computing device 52 can create a signal instructing the actuator 12 to move the moveable contact to the new location 14b that represents the theoretically-optimal location. In other instances, an element other than the computing device 52 (e.g., a doctor) can instruct/signal/actuate the actuator 12 to move the moveable contact to the new location.

In some instances, the computing device 52 can create the patient-specific computer model based on one or more imaging studies of an area of implantation of the lead assembly 10. In the images, the lead assembly 10 can be visible, as well as the neighboring anatomy. The patient-specific computer model 54 can take into account the anatomical features of the patient near the area of lead implantation. The theoretically-optimal location of the moveable contact can be determined based on the anatomical features. For example, the theoretically-optimal location of the moveable contact can reduce the amount of unintended stimulation, while increasing the amount of intended stimulation, thereby maximizing the clinical effect. After the position of the moveable contacts is set as the theoretically-optimal location, feedback (e.g., based on functional imaging or structural imaging) can be received and the moveable contacts can be re-positioned at a new theoretically-optimal location.

Figure 6:
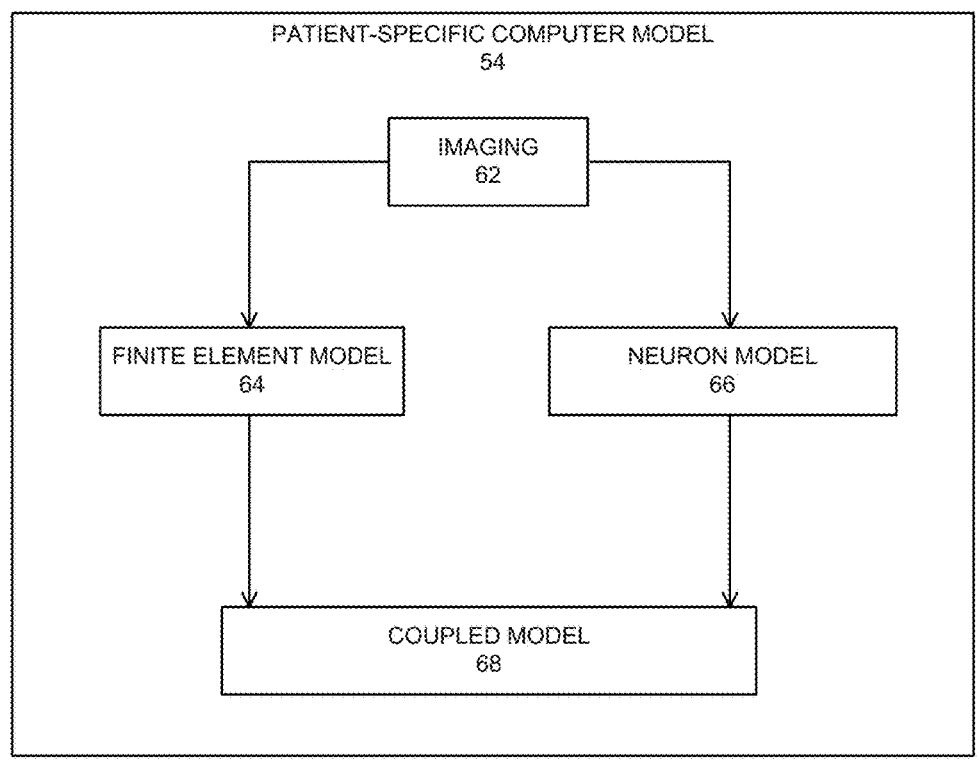
FIG. 6 is an example of the patient-specific model of FIG. 5.

As illustrated in FIG. 6, the patient-specific computer model 52 can include one or more sub-models. The patient-specific computer model 54 can include one or more of the sub-models and need not include all of the sub-models. In some instances, the patient-specific model can include a neuron model 64 that includes axon trajectories (e.g., in three-dimensions). The neuron model 64 can be determined based on one or more imaging studies 62. In other instances, the patient-specific model can include a finite element model that can be used to determine the areas stimulated by the moveable contact. The finite element model 66 can be determined based on one or more imaging studies 62. In still other instances, the patient-specific model can include a coupled finite element model-neuron model 68 that can illustrate the axons stimulated with a particular contact configuration. The axons stimulated can also depend on the stimulation pattern delivered by the particular contact configuration. Each of the sub-models individually or in combination can be used to determine the theoretically-ideal location for the moveable contact.

Figure 7:
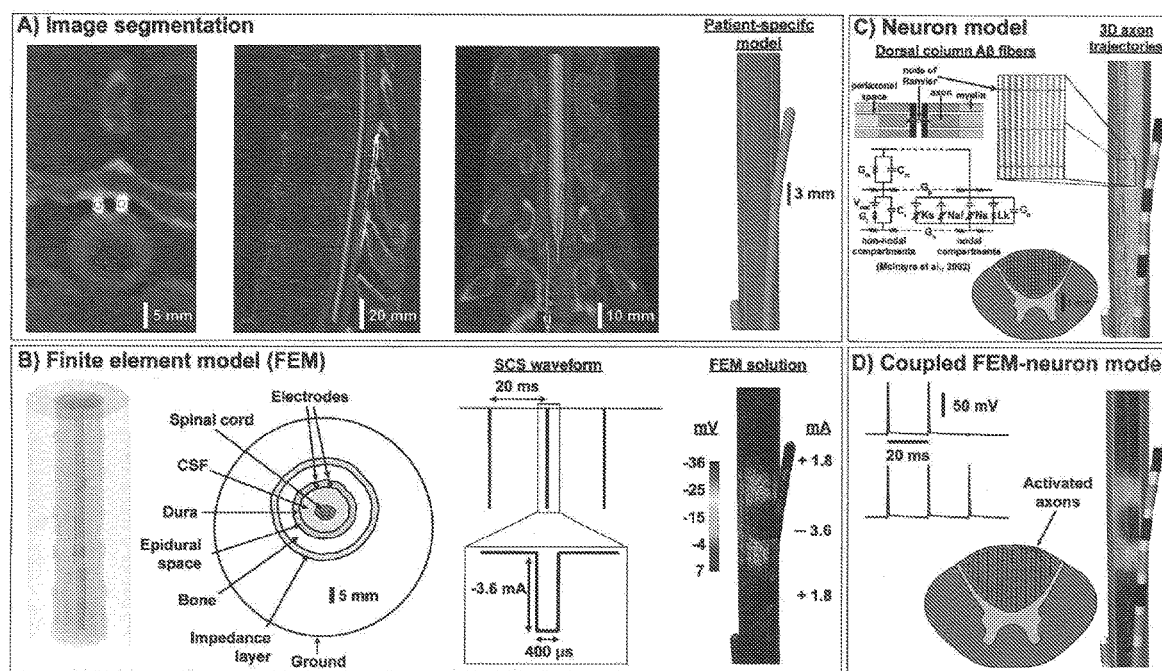
FIG. 7 shows a particular example of the patient-specific computer model of FIG. 6 with relation to spinal cord stimulation.

A particular example of the patient-specific computer model with relation to spinal cord stimulation with electrodes is shown in FIG. 7. An image can be taken of the portion of the patient with the implanted electrodes. In FIG. 7(A), image segmentation is performed to determine a patient-specific anatomy and electrode locations. In FIG. 7(B), a finite element model (FEM) is generated from the image segmentations and a voltage distribution is calculated for the desired stimulus parameter. In FIG. 7(C), multi-compartment neural models are placed within the appropriate patient anatomy. In FIG. 7(D), the FEM voltage distribution is coupled to the neural elements to estimate their response to SCS.

V. Methods

Figure 8:
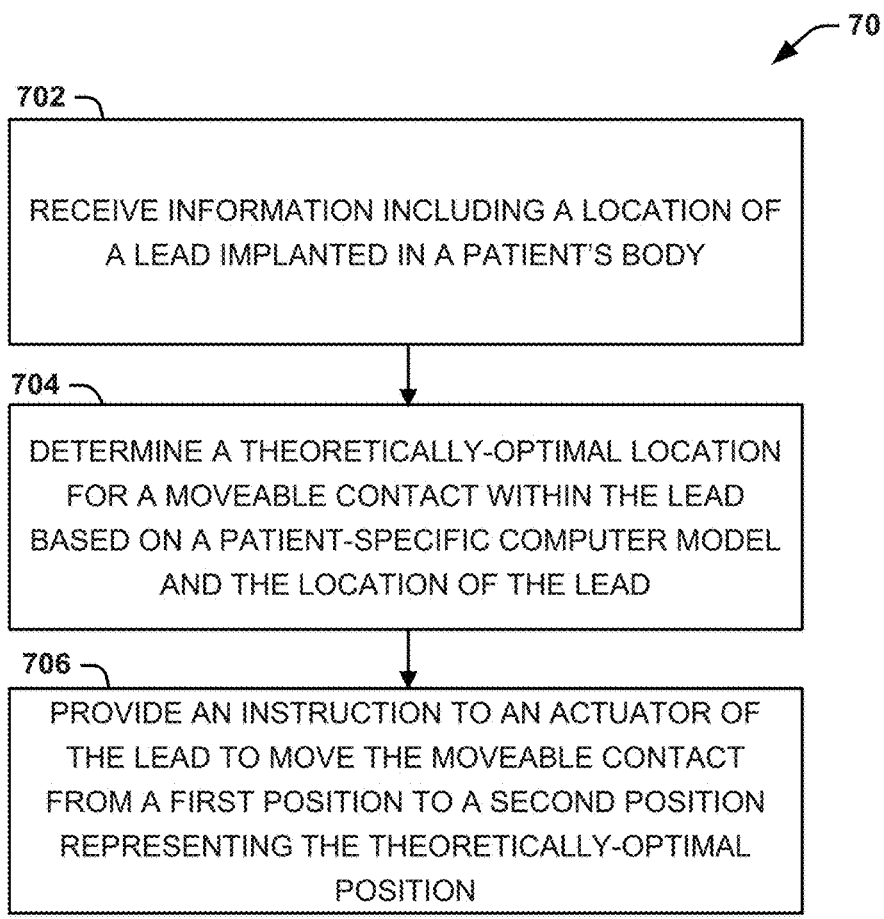
FIG. 8 is a process flow diagram of a method for re-positioning a contact of a lead assembly, according to another aspect of the present disclosure.
Figure 9:
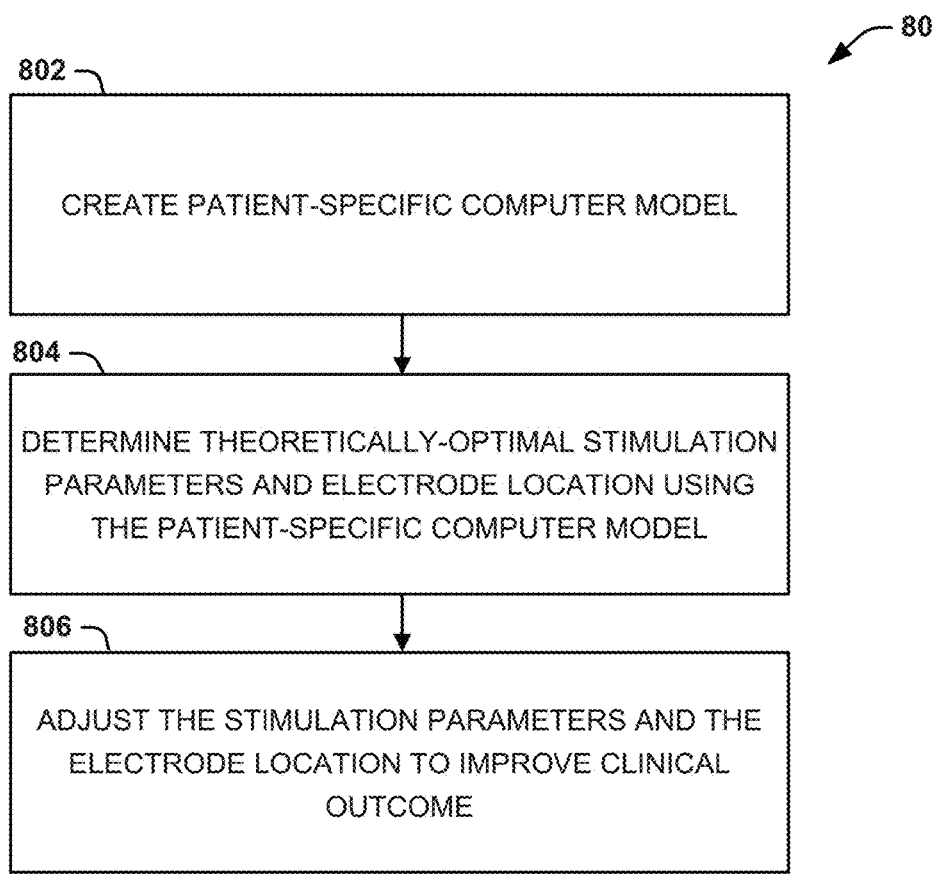
FIG. 9 is a process flow diagram of a method for determining theoretically-optimal stimulation parameters and contact positions that can be re-positioned according to the method of FIG. 7.

A further aspect of the present disclosure can include methods for moving at least one contact of a lead assembly that is implanted within a patient's body. FIG. 8 illustrates a method 70 for re-positioning a contact of a lead assembly. FIG. 9 illustrates a method 80 for determining theoretically-optimal stimulation parameters and contact positions that can be re-positioned according to the method 70.

The methods 70 and 80 are illustrated as a process flow diagram with flowchart illustrations. For purposes of simplicity, the methods 70 and 80 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 70 and 80.

One or more blocks of the respective flowchart illustrations, and combinations of blocks in the block flowchart illustrations, can be implemented by computer program instructions. These computer program instructions can be stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, the steps/acts can be implemented by a system comprising a processor that can access the computer-executable instructions that are stored in a non-transitory memory.

The methods 70 and 80 of the present disclosure may be embodied in hardware and/or in software (including firmware, resident software, micro-code, etc.). Furthermore, aspects of the present disclosure may take the form of a computer program product on a computer-usable or computer-readable storage medium having computer-usable or computer-readable program code embodied in the medium for use by or in connection with an instruction execution system. A computer-usable or computer-readable medium may be any non-transitory medium that can contain or store the program for use by or in connection with the instruction or execution of a system, apparatus, or device.

Referring now to FIG. 8, illustrated is a method 70 for re-positioning a contact of a lead assembly, as illustrated in FIGS. 1-4, after implantation in a patient's body after healing and, in some instances, the development of scar tissue. However, in some instances, the lead assembly 10 can be covered, in at least a portion, by a film that prevents scar tissue from being formed around the lead assembly 10. At 702, information can be received, including a location of a lead implanted in a patient's body. For example, the information can be received from one or more imaging studies of the patient's body. The imaging studies can include the area of implantation so that the lead assembly is visible, as well as the neighboring anatomy. Based on the imaging studies, positions for the contacts of the lead assembly can be studied based on the location of the lead, and, in some instances, the anatomy surrounding the location of the lead.

At 704, a theoretically-optimal location for the moveable contact within the lead can be determined based on a patient-specific model and the location of the lead. The determination can be done before and/or after implantation of the lead (e.g., before surgical incisions closed, after surgical incisions closed, after healing from the surgical incisions and the development of scar tissue). For example, the patient-specific model can be created based on the imaging studies and can include the location of the lead. The patient-specific model can take into account the anatomical features of the patient near the area of lead implantation. In some instances, the patient-specific model can include a neuron model that includes axon trajectories (e.g., in three-dimensions). In other instances, the patient-specific model can include a finite element model that can be used to determine the areas stimulated by the moveable contact. In still other instances, the patient-specific model can include a coupled finite element model-neuron model that can illustrate the axons stimulated with a particular contact configuration. The axons stimulated can also depend on the stimulation pattern delivered by the particular contact configuration.

At 706, an instruction (e.g., an encoded instruction) can be provided to an actuator of the lead to move the moveable contact from a first position to a second position representing the theoretically-optimal position. In some instances, the instruction can be an encoded instruction from the system comprising the processor. In other instances, the instruction can be from something external to the system (e.g., a user viewing an output of the system). The actuator can be coupled to the moveable contact and can activate the motion of the moveable contact from the first position to the second position. In some instances, the actuator can be a piston/cylinder mechanism, a pneumatic actuator, a piezoelectric actuator, a hydraulic actuator, a shape memory actuator, or an electro-mechanical actuator.

Referring now to FIG. 9, illustrated is a method 80 for determining theoretically-optimal stimulation parameters and contact positions. At 802, a patient-specific computer model can be created. For example, the patient-specific computer model can be created based on one or more imaging studies of an area of implantation of the lead assembly. The lead assembly can be visible, as well as the neighboring anatomy. The patient-specific model can take into account the anatomical features of the patient near the area of lead implantation. In some instances, the patient-specific model can include a neuron model that includes axon trajectories (e.g., in three-dimensions). In other instances, the patient-specific model can include a finite element model that can be used to determine the areas stimulated by the moveable contact. In still other instances, the patient-specific model can include a coupled finite element model-neuron model that can illustrate the axons stimulated with a particular contact configuration. The axons stimulated can also depend on the stimulation pattern delivered by the particular contact configuration.

At 804, the theoretically-optimal stimulation parameters and electrode location can be determined using the patient-specific computer model. The patient-specific computer model can be used to minimize stimulation of unintended areas whole maximizing stimulation of intended areas. The minimization and maximization can be determined, for example, based on results of the coupled finite element model-neuron model that can illustrate the axons stimulated with a particular contact configuration and particular stimulation parameters. In some instances, the intended and unintended areas of the body can be distinguishable in the model (e.g., displayed in different colors, different lines, or another type of distinguishable display). At 806, the stimulation parameters and the electrode location can be adjusted to improve clinical outcome. The minimization of the stimulation of the unintended areas and maximization of stimulation of the intended areas can lead to a more effective treatment for the patient.

From the above description, those skilled in the art will perceive improvements, changes and modifications. Such improvements, changes and modifications are within the skill of one in the art and are intended to be covered by the appended claims.

What is claimed is:

1. A method comprising:
receiving, by a system comprising a processor, information comprising a location of a lead in a patient's body;
determining, by the system, a theoretically-optimal location for a moveable contact within the lead that maximizes a clinical effect of stimulating the tissue based on a patient-specific computer model and the location of the lead, wherein the patient-specific computer model is created based on one or more imaging studies; and
providing an instruction to an actuator of the lead to move the moveable contact from a first position to a second position representing the theoretically-optimal location,
wherein the actuator is in operable communication with at least one of a first lead body and a second lead body of the lead to cause sliding relative movement between the lead bodies, which results in movement of the moveable contact from the first position to the second position.

2. The method of claim 1, wherein the lead comprises a first lead body comprising a first slot arranged in a first orientation and a second lead body comprising a second slot corresponding to the first slot and having a second orientation, the first lead body slidably coupled to the second lead body, wherein the moveable contact is moveably disposed in the first slot and the corresponding second slot.

3. The method of claim 2, wherein the first orientation is different from the second orientation.

4. The method of claim 3, wherein the first orientation is substantially diagonal and the second orientation is substantially horizontal.

5. The method of claim 1, further comprising determining, by the system, a stimulation parameter to be applied by the moveable contact based on the patient-specific computer model.

6. The method of claim 1, further comprising defining, by the system, the patient-specific computer model based on neuron location determined based on one or more images of the lead after implantation and at least one of a finite element model, a neuron model, and a coupled model based on the location of the lead and one or more stimulation parameters.

7. The method of claim 1, wherein the actuator comprises at least one of a piston/cylinder mechanism, a pneumatic actuator, a piezoelectric actuator, a hydraulic actuator, a shape memory actuator, and an electro-mechanical actuator.

8. The method of claim 1, further comprising creating, by the system, the patient-specific computer model based on one or more imaging studies.

9. The method of claim 1, wherein the lead comprises a flexible material.

10. The method of claim 9, wherein the flexible material comprises nitonol.

* * * * *